(12) United States Patent
Drewry et al.

(10) Patent No.: US 7,867,258 B2
(45) Date of Patent: Jan. 11, 2011

(54) MULTI-AXIAL BONE ATTACHMENT MEMBER

(75) Inventors: Troy D. Drewry, Memphis, TN (US); William B. Null, Olive Branch, MS (US); Marc T. Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 597 days.

(21) Appl. No.: 11/581,812

(22) Filed: Oct. 17, 2006

(65) Prior Publication Data

US 2008/0177321 A1    Jul. 24, 2008

(51) Int. Cl.
*A61B 17/70*    (2006.01)
(52) U.S. Cl. .................. 606/266; 606/269; 606/305
(58) Field of Classification Search .............. 606/61, 606/264–364; 411/8–14
See application file for complete search history.

(56) References Cited

U.S. PATENT DOCUMENTS

| | | | |
|---|---|---|---|
| 5,466,237 A | 11/1995 | Byrd, III et al. | |
| 5,474,555 A | 12/1995 | Puno et al. | |
| 5,549,608 A | 8/1996 | Errico et al. | |
| 5,586,984 A | 12/1996 | Errico et al. | |
| 5,669,911 A | 9/1997 | Errico et al. | |
| 5,728,098 A | 3/1998 | Sherman et al. | |
| 5,797,911 A | 8/1998 | Sherman et al. | |
| 5,863,293 A | 1/1999 | Richelsoph | |
| 5,879,350 A | 3/1999 | Sherman et al. | |
| 5,885,286 A | 3/1999 | Sherman et al. | |
| 6,280,442 B1 * | 8/2001 | Barker et al. ............ | 606/60 |
| RE37,665 E | 4/2002 | Ralph et al. | |
| 6,579,292 B2 | 6/2003 | Taylor | |
| 6,964,666 B2 * | 11/2005 | Jackson ................ | 606/308 |
| RE39,089 E | 5/2006 | Ralph et al. | |
| 7,066,937 B2 | 6/2006 | Shluzas | |
| 7,087,057 B2 | 8/2006 | Konieczynski et al. | |
| 7,144,396 B2 | 12/2006 | Shluzas | |
| 7,604,656 B2 | 10/2009 | Shluzas | |
| 7,682,377 B2 | 3/2010 | Konieczynski et al. | |
| 2006/0084981 A1 | 4/2006 | Shluzas | |
| 2006/0089644 A1 * | 4/2006 | Felix ...................... | 606/61 |
| 2006/0276789 A1 * | 12/2006 | Jackson ................ | 606/61 |
| 2008/0015576 A1 | 1/2008 | Whipple | |

* cited by examiner

*Primary Examiner*—Eduardo C Robert
*Assistant Examiner*—Christina Negrelli

(57) ABSTRACT

Orthopedic constructs having parts that are movable with respect to each other and one or more friction members to limit unintended movement are disclosed. In one embodiment, a multi-axial bone anchor having a receiver member and a screw-type anchor is provided. The receiver member includes one or more internal apertures in which a friction member is placed, and a portion of the anchor contacts or is loosely held by the friction member(s).

25 Claims, 2 Drawing Sheets

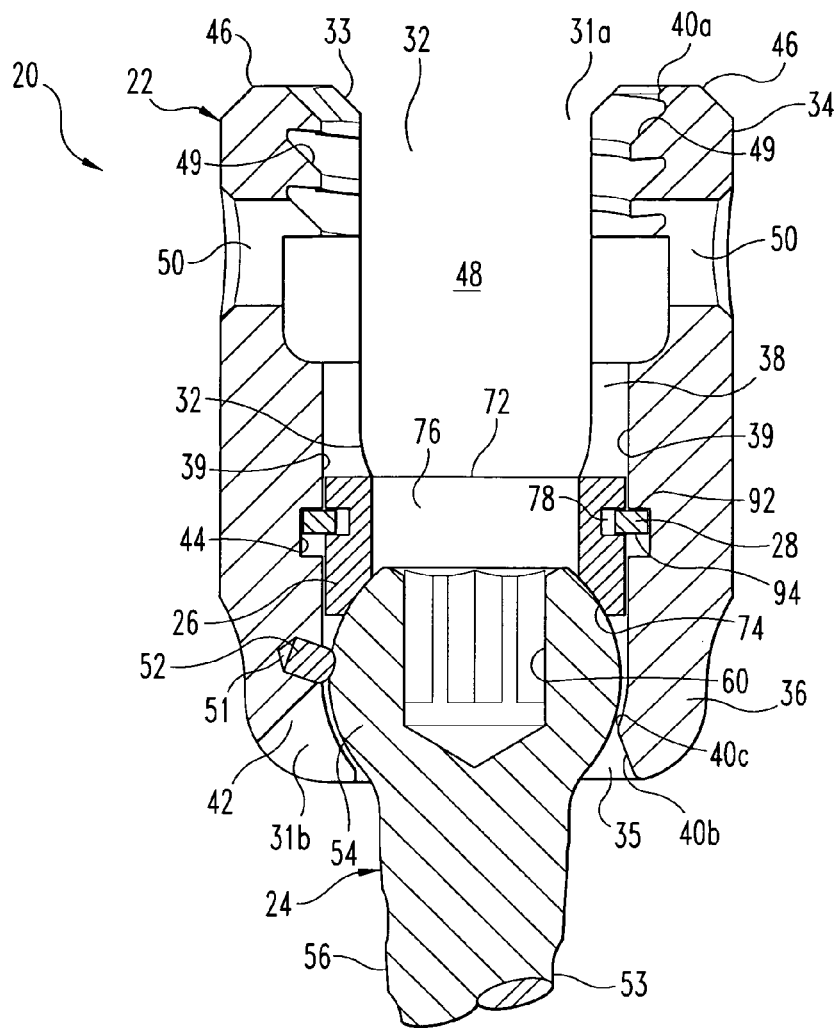
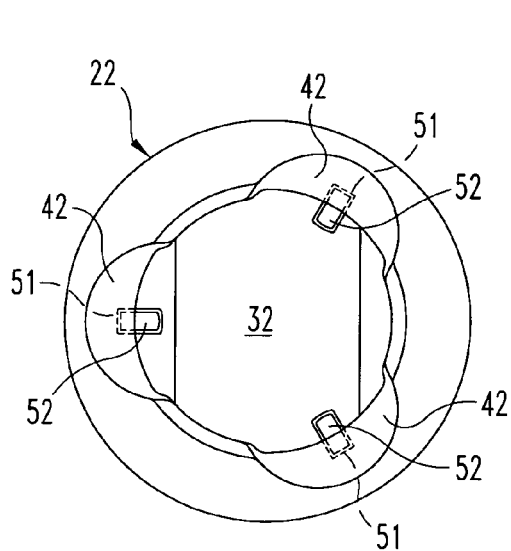
Fig. 3
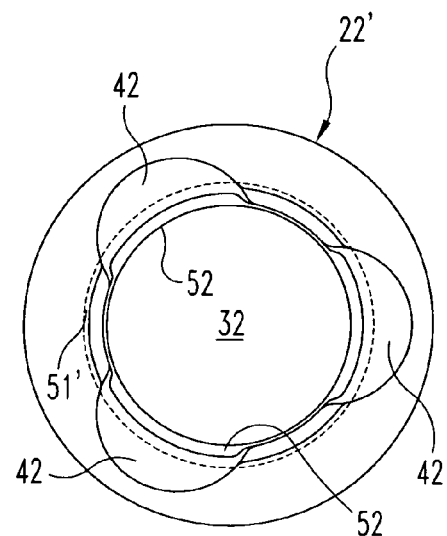
Fig. 3A

MULTI-AXIAL BONE ATTACHMENT MEMBER

The present disclosure relates to devices and implants used in osteosynthesis and other orthopedic surgical procedures. Specifically, the present disclosure contemplates orthopedic devices such as bone anchor assemblies having parts capable of moving with respect to each other in a limited fashion.

Numerous implant devices that have two or more parts that can move with respect to each other are known for use in orthopedic surgical procedures. For example, in the spinal context techniques and systems have been developed for connecting a correcting and/or stabilizing rod or other elongated member to vertebrae via multi-axial bone anchors. In using such bone anchors or other implants or pieces that have parts that can move relative to each other, at times such items can be difficult for a surgeon to handle due to such relative movement. In the case of multi-axial bone anchors, for example, if the surgeon picks up such an anchor by one part, another part of it may move to an inconvenient location or position. In that situation, additional time and/or instruments may be required to hold and position the parts of the implant for proper use.

BRIEF DESCRIPTION OF THE DRAWINGS

FIG. 2 is a medial cross sectional view of the embodiment of the depicted in FIG. 1 and in the same orientation as in FIG. 1.

FIG. 3 is a bottom plan view of the embodiment illustrated in FIG. 1.

FIG. 3A is a bottom plan view of an implant apparatus having aspects similar to the embodiment of FIG. 1.

DESCRIPTION OF THE ILLUSTRATED EMBODIMENTS

Figure 1:
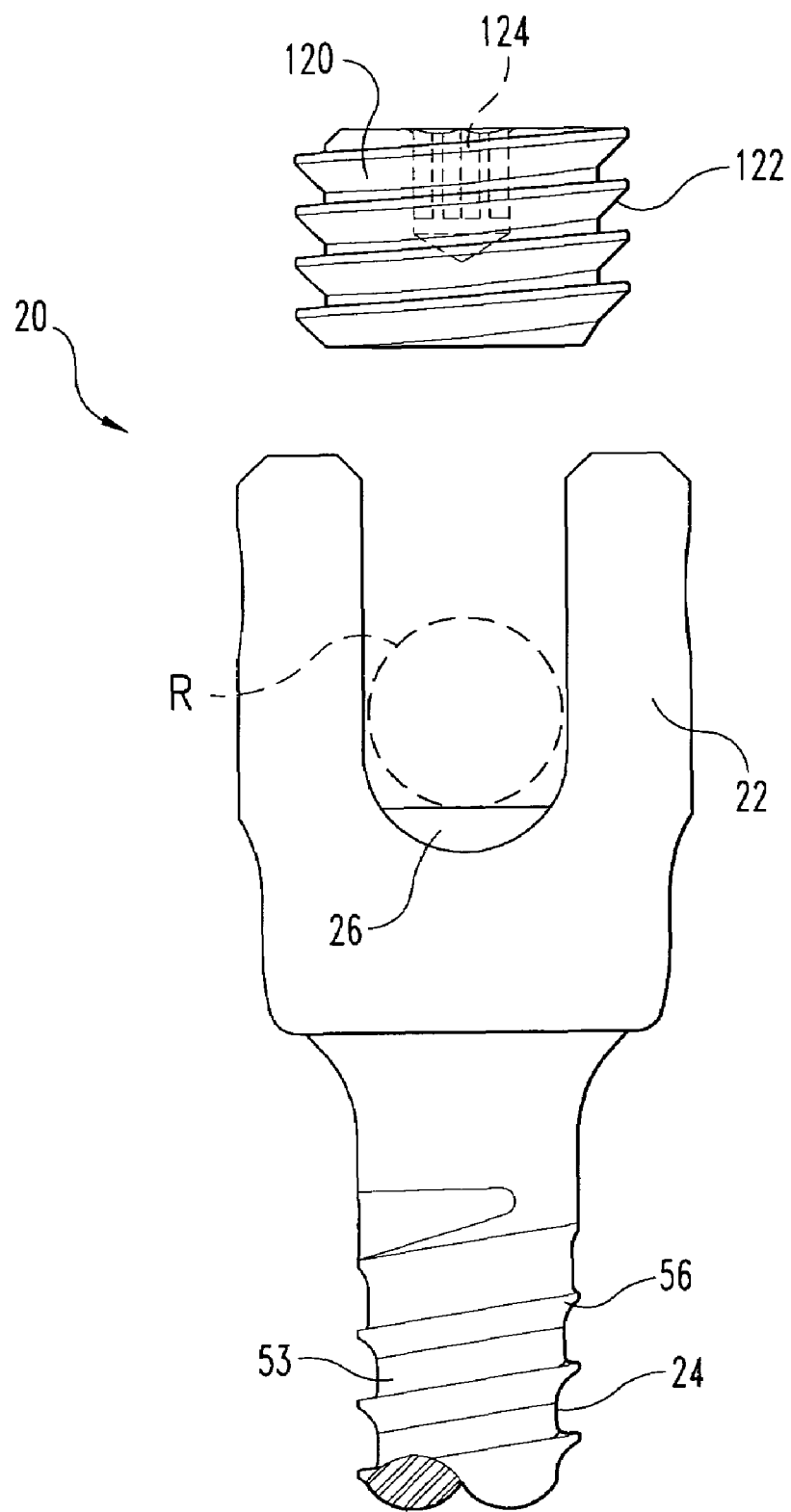
FIG. 1 is a side elevational view of one embodiment of an implant apparatus.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring generally to the figures, there is shown one embodiment of a multi-axial orthopedic assembly 20 of the present disclosure. In that illustrated embodiment, assembly 20 includes a receiver member 22, a bone anchor 24, a crown member 26, and a retaining member 28. The assembly 20 of the present disclosure is designed for use with an elongated member R such as a spinal rod, bar or other orthopedic construct, as further described below. It will be seen that aspects of the present disclosure may be used with a variety of orthopedic assemblies having parts that move with respect to each other.

The illustrated embodiment of receiver member 22 defines an upper opening portion 31a and a lower opening portion 31b, which in the illustrated embodiment form a single opening 32 extending through receiver member 22 from an upper aperture 33 in top portion 34 to a lower aperture 35 in bottom portion 36. Lower opening portion 31b of opening 32, in one specific embodiment, includes a chamber 38 defined by a chamber wall 39. Alternatively, upper and lower opening portions 31a, 31b can have a variety of configurations, such as each having one or more sections of differing diameter.

Opening 32 is partially surrounded by a chamfered or rounded edge 40a at or near top portion 34 of receiver member 22, and is partially surrounded by a relatively external chamfered or rounded edge 40b and a relatively internal chamfered or rounded edge 40c at or near the bottom portion 36 of receiver member 22. Edge 40c may be sharp in other embodiments to contact anchor 24 substantially along an arc or other line. Lower opening portion 31b may have at least one part 42 that is open at least somewhat toward one side of receiver member 22, and in the illustrated embodiment three such parts 42 are shown equiangularly spaced around lower opening portion 31b. It will be seen that if multiple parts 42 are provided, they may be asymmetrically arranged. A groove 44 is defined in wall 39 around opening 32. In the illustrated embodiment, groove 44 extends around the entire perimeter of opening 32, although it will be seen that groove 44 could extend only partially around the perimeter of opening 32. Further, the illustrated embodiment of receiver member 22 shows groove 44 approximately halfway along wall 39 measured top-to-bottom, although groove 44 could be positioned further toward either of upper aperture 33 or lower aperture 35. Groove 44 has a groove depth measured from wall 39 to a wall of the groove substantially parallel to wall 39, and a groove diameter measured across opening 32.

Receiver member 22 in the illustrated embodiment includes a pair of upright branches 46 through which opening 32 extends. Branches 46 further define a U-shaped channel 48 transverse to opening 32 that communicates with upper portion 31a and lower portion 31b of opening 32, and that can accommodate an elongated member such as rod R. Channel 48 is sized to accommodate any of a variety of rods or other elongated members, whether of relatively large or relatively small diameter, so long as such members fit within channel 48. In a specific embodiment, internal threads 49 are formed in branches 46, and branches 46 are provided with indentations or holes 50, which allow the surgeon to grip receiver member 22 with an appropriate tool (not shown). Thread 49 ends above the point to which the largest rod R compatible with receiver member 22 (e.g., a rod with a diameter substantially equal to the internal distance between branches 46) could extend, as indicated by the internal gap in branches 46 between thread 49 and chamber 38. Thread 49 in a specific embodiment is a reverse angle thread, i.e. a thread in which the forward or pressure flank points down and in toward receiver member 22, as disclosed in commonly-owned U.S. Pat. No. 6,296,642, the disclosure of which is hereby incorporated by reference.

Receiver member 22 also includes one or more apertures 51 located toward or in bottom portion 36. As shown in the illustrated embodiment, three apertures 51 are located substantially in the same plane (i.e. about the same distance above aperture 35 of member 22) and equiangularly spaced around chamber 38 and opening 32. The illustrated embodiment also shows apertures 51 to be oriented obliquely to opening 32, slanting upward as one moves from the interior of receiver member 22 toward its exterior. In other embodiments, apertures 51 could be substantially perpendicular to opening 32 or oblique and downward-slanting. In one particular embodiment, aperture(s) 51 are placed in receiver member 22 so that they are adjacent to the widest part of anchor 24. It will be seen that in other embodiments, different numbers, spacings, placement and/or orientations of aperture (s) 51 may be included. As examples, a single aperture 51 or two apertures 51 or more than three apertures 51 may be included; one or two apertures 51 may be placed substantially underneath one of branches 46; or two apertures 51 may be substantially underneath one branch 46 and one aperture 51 may be substantially underneath another branch 46. Further, the illustrated embodiment of receiver member 22 includes apertures 51 that are substantially cylindrical in form, and extend approximately half-way from wall 39 to an exterior surface of receiver member 22. In other embodiments, aperture(s) 51 could be otherwise shaped, or of other depths. As one example, indicated in FIG. 3A, an aperture 51' could be configured as a groove in wall 39 separate from groove 44.

Insert material 52 is placed at least partially within one or more of aperture(s) 51 of receiver member 22. Insert material 52 extends at least minimally past wall 39 and into opening 32 of receiver member 22, forming a rounded or part-spherical bead surface in the illustrated embodiment. Insert material 52, in the illustrated embodiment, is a substance that is biocompatible, at least substantially solid at or near room and body temperature, and has a relatively high friction coefficient. Insert material 52 may be substantially non-compressible, or may be relatively easily compressed. Such substances may include natural or artificial rubbers, cured silicon adhesives or other silicon products, polyurethanes, polyethylene, additional polymers that have elastomeric properties to apply force when put under compression, or other substances. In certain embodiments, insert material 52 may be considered to be analogous to a pencil eraser insofar as it extends from a substantially cylindrical hole and is of a relatively high friction material. Concerning embodiments like FIG. 3A, material 52 may form a complete or partial ring in groove-shaped aperture 51'. In other embodiments, relatively flat areas, beads, or other configurations of adhesive may be applied to receiver member 22, and anchor 24 can be attached to the adhesive, so that a firm connection between receiver member 22 and anchor 24 that is easily broken by a surgeon is formed. As discussed further below, material 52 acts to increase the friction between two parts of assembly 20, e.g. receiver member 22 and anchor 24, so as to make movement between the parts possible but more resisted than if material 51 were not present. Material 52 may be considered a friction member that loosely holds or limits or prevents unintended movement of anchor 24, as further described below.

The illustrated anchor 24 is a bone screw, while in other embodiments anchor 24 could be a hook, clamp or other appropriate anchoring member. Anchor 24 includes an anchorage portion 53 and a head portion 54. Anchorage portion 53, in the embodiment in which anchor 24 is a screw, includes at least one thread 56, which may be a cancellous self-tapping thread. Head portion 54 forms part of a relatively smooth sphere in the illustrated embodiment, though alternative curvate and other configurations may be employed. Head 54 could include a series of concentric, linear or other ridges (not shown) for improving purchase with the inside of crown member 26 (described below). Head 54 may have additional or alternative friction-increasing surface configuration(s) such as roughening or knurling. Further, head 54 includes a tool-engaging print 60, with which a tool (not shown) may be engaged to drive anchorage portion 52 into a bone. Tool-engaging print 60 is an interior print in the illustrated embodiment, although an exterior print could be used, and it may have any of a number of configurations, such as hexagonal, hexalobate, or other known torque-transferring configurations.

Other embodiments of bone anchor 24 are contemplated as being within the scope of the present disclosure, as noted above. For example, anchor 24 could be a bone-engaging hook. In that embodiment, anchorage portion 52 could be configured with a blade or similar part forming a hook, rather than an elongated section with thread 56.

Head 54 of anchor 24 is shaped and sized to fit within at least lower portion 31*b* of opening 32 and chamber 38 of receiver member 22. The illustrated embodiment shows head 54 with a diameter at least slightly larger than lower aperture 35, so that head 54 can abut surface 40*c* and portions of insert material or friction members 52. In that embodiment, anchor 24 may be inserted into upper aperture 33 and through opening 32 so that anchor portion 53 extends from lower aperture 35, and friction members 52 may be at least approximately along a diameter or great circle of head 54. In other embodiments, head 54 may have a width smaller than the width of lower aperture 35, and may be bottom loaded with an auxiliary piece maintaining head 54 at least partially within receiver member 22.

In the illustrated embodiment, crown member 26 is in the shape of a substantially circular disc, having an upper surface 72 and a lower surface 74. Lower surface 74 is configured to accommodate at least a portion of head 54 of anchor 24, and therefore the illustrated embodiment of lower surface 74 has the shape of part of a sphere. Alternatively or additionally, lower surface 74 of crown member 26 could have one or more other shapes, such as a beveled or conical lower surface. Lower surface 74 can be provided with a friction- or purchase-enhancing surface configuration (e.g. roughening or knurling) for cooperation with head 54 of bone anchor 24. The illustrated embodiment of crown member 26 also includes a hole 76 and groove 78. Hole 76 is provided so that head 54, and in particular embodiments tool-engaging print 60, of anchor 24 may be accessed through crown member 26. Groove 78 is in an external side surface of crown member 26, and in the illustrated embodiment extends around the entire circumference or perimeter of crown member 26. In other embodiments, a single or multiple grooves 78 may extend around part or all of the circumference or perimeter of crown member 26. Crown member 26 is sized and shaped to fit within at least lower portion 31*b* of opening 32 and chamber 38 of receiver member 22, and in the illustrated embodiment is substantially circular. An outer dimension of crown member 26 may be slightly smaller than an inner dimension of chamber 38 and lower portion 31*b* of opening 32 so that crown member 26 is slidably and rotatably movable within at least a portion of chamber 38 and opening 32.

In the illustrated embodiment, retaining member 28 is a C-shaped spring or clip that forms most of a circle. In other embodiments, retaining member 28 may be about half or less of a circle, may be an entire circle (e.g. a washer-type member), or may have another shape useful with the particular configuration of one or both of grooves 44 and 78. The illustrated embodiment of retaining member 28 is also approximately square in cross-section, having relatively sharp edges on a top surface 92 and a bottom surface 94. Other cross-sectional shapes are also possible, such as rectangular or irregular. In embodiments in which retaining member 28 is a C-shaped ring or clip, retaining member 28 may have an unloaded or natural outer diameter, i.e. a diameter measured when retaining member 28 is under no contractive or expansive stress. Such an unloaded diameter of retaining member 28, in one embodiment, is slightly larger than the groove diameter of groove 44, so that when retaining member is in groove 44, retaining member 28 presses against receiver member 22. In other embodiments, retaining member 28 may have an unloaded diameter that is between the diameters of grooves 44 and 78. Further, retaining member 28 may have a body width that is substantially constant, and that is greater than the depth of grooves 44 and/or 78.

The illustrated embodiment of assembly 20 is assembled as follows. Anchor 24, crown member 26 and retaining member 28 are inserted into receiver member 22 through top portion 34 and bottom portion 36, either individually or substantially in one step. For example, anchor 24 may be inserted first so that head 54 is adjacent or abutting friction member(s) 52, followed by crown member 26 with retaining member 28 in or adjacent to groove 78 of crown member 26. Retaining member may be squeezed by wall 39 until retaining member 28 is at least partially within groove 44. Crown member 26 rests atop head 54 of anchor 24. By placing crown member 26 atop head 54 of anchor 24, so that lower surface 78 of crown member 26 adjoins head 54, and fitting crown member 26 and retaining member 28 together as described above, simultaneous insertion of anchor 24, crown member 26 and retaining member 28 into receiver member 22 may be accomplished. However and in whatever order anchor 24, crown member 26 and retaining member 28 are inserted into receiver member 22, the result in the illustrated embodiment is to have a portion of retaining member 28 in each of grooves 44 and 78, and head 54 of anchor 24 between crown member 26 and lower opening 35 of receiver member 22.

Crown member 26 remains slideably and rotatably positioned in chamber 38 and opening 32 of receiver member 22, and anchor 24 remains multi-axially moveable with respect to crown member 26 and receiving member 22. Head 54 of anchor 24 abuts insert material or friction member 52 in apertures 51 in receiver member 22. The relatively high-friction contact between head 54 and material 52 keeps anchor 24 from moving substantially with respect to receiver member 22 unless particular force is applied to one of receiver member 22 and anchor 24. Thus, if a surgeon or another person holds receiver member 22 only, anchor 24 does not "flop around" or move substantially with respect to receiver member 22, unless the person forces them to move with respect to each other. In certain embodiments, material 52 has a high enough coefficient of friction and head 54 is wedged or firmly pressed against one or more placements of material 52, so that anchor 24 may move very slightly, if at all, when the surgeon holds only receiver member 22. However, if repositioning of receiver member 22 and anchor 24 is desired, then one of receiver member 22 and anchor 24 can be held while the other is rotated, pivoted, or otherwise moved. For example, if the surgeon wishes for receiver member 22 and anchor 24 to be oriented in a particular fashion, then he or she can hold receiver member 22 and move anchor 24 against the resistance of the material 52 between receiver member 22 and anchor 24, until anchor 24 and receiver member 22 are oriented as he or she desires.

As noted above, in one specific embodiment the groove diameter of groove 44 is smaller than the outer diameter of retaining member 28 in its natural (i.e., unloaded) condition. Thus, when retaining member 28 is within groove 44, retaining member 28 presses against the walls of groove 44. Alternatively, the diameter of groove 44 may be the same size or slightly larger than the natural outer diameter of retaining member 28. In that case, a portion of retaining member 28 rests in groove 44 without exerting appreciable force on receiver member 22. The depth of groove 44 is less than the width of retaining member 28, so that when retaining member 28 is in groove 44, a portion of retaining member 28 projects into opening 32. When retaining member 28 is at least partially within groove 44, crown member 26 is retained within opening 32 of receiver member 22, and in the illustrated embodiment crown member 26 remains in a certain area of receiver member 22. Crown member 26 is above or atop head 54 of anchor 24, and head 54 is supported by internal surface 40c of receiver member 22.

Assembly 20 may be assembled (e.g., as described above) prior to use in a surgical procedure. In using the illustrated embodiment of assembly 20, anchor 24 of assembly 20 is threaded into an appropriately prepared hole in a bone (not shown). It will be understood that in alternative embodiments of the disclosure, for example where anchor 24 is a hook, drilling a hole in bone and threading an anchor therein may not be necessary. Threaded anchoring portion 52 is inserted into the hole, and an appropriate screwing tool is used with tool-engaging print 60 of anchor 24 through hole 76 in crown member 26, and anchor 24 is threaded into the bone. During such threading, receiver member 22 may turn with anchor 24 due to the frictional contact of a portion of anchor 24 (e.g. head 54) with material 52 in receiver member 22. If the surgeon does not desire that anchor 24 and receiver member 22 turn together during the threading, he or she may hold receiver member 22 while turning anchor 24.

When anchor 24 has been threaded into the bone to a desired depth, receiver member 22 can be turned, pivoted, or otherwise moved or positioned so that opening 32 and channel 48 forms a desired angle with bone anchor 24. There will be, in most cases, some amount of resistance to such movement or positioning of receiver member 22 with respect to anchor portion 24 due to friction member(s) 52. In one particular embodiment, the angle between anchor 24 and opening 32 can be any value up to 35 degrees in any direction, and when anchor 24 is pointed toward an open portion 42 of lower opening 31b of receiver portion 22, the angle may be substantially greater, for example about 50 degrees or more depending on the diameter of the anchor 24 (e.g. 60 degrees). It will be seen that the maximum angle of anchor 24 relative to opening 32 can be changed in several ways, for example by thinning the portion of anchor 24 beneath head 54, or by providing steeper angulation of edge 40b and/or open portion 42.

As described above, receiver member 22 may be angled as the surgeon desires with respect to bone anchor 24. An elongated member R such as a spinal rod, connector, or other orthopedic surgical implant is coupled with assembly 20. Elongated member R is placed in channel 48 of receiver member 22, and contacts crown member 26. A compression member 120, is inserted into receiver member 22 and down onto elongated member R. Compression member 120, in the illustrated embodiment, is a set screw or plug having external threads 122 compatible with threads 49 of receiver member 22 and a print 124 for applying torque. In other embodiments, the compression member may be all or part of a break-off set screw as disclosed in U.S. Pat. No. 5,885,286 to Sherman et al., incorporated herein by reference. In certain embodiments, thread 122 may be a reverse angle thread as disclosed in U.S. Pat. No. 6,296,642, incorporated herein by reference. Alternatively, in embodiments in which receiver member 22 is externally threaded, compression member 120 could be an internally-threaded nut.

As compression member 120 is tightened, elongated member R is forced downward against crown member 26, which pushes crown member 26 down onto head 54 of anchor 24. Head 54 is thereby clamped between crown member 26 on top, and relatively internal surface 40c of receiver member 22, and perhaps material 52, on the bottom. In embodiments in which head 54 includes ridges or other roughened portions, such ridges or roughened portions are pressed into and may penetrate into lower surface 74 of crown member 26. Accordingly, anchor 24 is locked into a desired angular position with respect to elongated member R and the remainder of assembly 20.

Receiver member 22, anchor 24, crown member 26 and retaining member 28 may be made out of stainless steel, titanium, ceramics, certain hard plastics, or other sturdy biocompatible materials. The various parts may all be made of the same material. In one specific embodiment, crown member 26 may be made of a material somewhat softer than the material used for head 54 of bone anchor 24, so that crown member may be deformed (or a portion of head 54 penetrate into crown member 26) somewhat more easily during locking of assembly 20, thereby providing a more definite purchase between head 54 and crown member 26. In another specific embodiment, crown member 26 may be made of a material somewhat softer than the material used for elongated member R. Such construction will allow crown member 26 to deform to the shape of elongated member R during locking of assembly 20, also providing a more secure locking of the implant. These parts allow elongated members of any of a variety of diameters, from diameters approximately the same as the internal distance between branches 46 to diameters significantly smaller, to be locked between branches 46 and between crown member 26 and retaining member 28.

In a particular embodiment, material 52 is inserted into apertures (e.g. apertures 51, 51') in a liquid, gel, or other curable state that exudes slightly from the apertures and forms a bead above the rim of the apertures. On curing, material 52 retains that bead shape and had characteristics substantially as discussed above. In other embodiments, suitable materials 52 may be provided in cured or substantially-cured form and inserted into the aperture(s) 51, 51'.

Although a multi-axial screw implant embodiment is described above, it will be seen that other types of implants or anchors can incorporate features described herein. For example, a hook, clamp or other type of anchor can be used in place of or in addition to screw-type anchor member 53 discussed above. Further, in addition to multi-axial screws or other anchors, anchors that rotate with respect to a receiver or other member (e.g. around a longitudinal axis of the anchor) and anchors that pivot in substantially a single plane with respect to a receiver or other member can include features described above. While a receiver member compatible with rods or similar elongated members is described above, the features described above can be used in connection with other orthopedic devices that have two parts that pivot, rotate, or otherwise move with respect to each other. Further, the structures described herein are useful with elongated members of any of a variety of diameters. Anchor members having heads of different diameters can also be used with embodiments of receiver member 22, since a compressible and friction-enhancing material 52 would enable anchors with somewhat smaller heads (relative to opening 32) than anchor 24 to be effectively used.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected.

What is claimed is:

1. An orthopedic implant apparatus comprising:
   a receiver member for receiving at least a part of a spinal rod, said receiver member having a lower opening and an internal chamber with a side wall defining an internal surface of said internal chamber, said receiver member further having at least one aperture in said side wall, and further including at least one friction member at least partially in at least one of said apertures, said friction member is comprised of a non-metallic elastomeric material; and
   an anchor member having a head portion defining an external surface and an anchor portion, said anchor member being movably connected to said receiver member with a portion of said external surface of said head portion abutting said internal surface of said receiver member, said head portion is comprised of a biocompatible material different from said elastomeric material and selected from the group consisting of a metallic material, a ceramic material and a hard plastic material, said non-metallic elastomeric material of said friction member abutting said external surface of said head portion so that unintended relative movement of said anchor member and said receiver member is substantially limited.

2. The apparatus of claim 1, further comprising a crown member slidably positioned in said internal chamber of said receiver member; and
   wherein said head portion of said anchor member adjacent said crown member; and
   wherein said friction member is positioned between said crown member and said lower opening of said receiver member.

3. The apparatus of claim 1, wherein said non-metallic elastomeric material is selected from the group consisting of a polymeric material, a rubber-based material, and a silicone-based material.

4. The apparatus of claim 1, wherein said biocompatible material comprises a metallic material.

5. The apparatus of claim 1, wherein said non-metallic elastomeric material forms a distal end face of said friction member and is positioned in abutment against said external surface of said head portion so that said unintended relative movement between said anchor member and said receiver member is substantially limited.

6. The apparatus of claim 5, wherein said external surface of said head portion includes a spherical-shaped surface with a portion of said spherical-shaped surface abutting said internal surface of said receiver member, said distal end face of said friction member positioned in abutment against said spherical-shaped surface of said head portion so that said unintended relative movement between said anchor member and said receiver member is substantially limited.

7. The apparatus of claim 5, wherein said distal end face of said friction member comprises a part-spherical bead surface positioned in abutment against a spherical-shaped portion of said external surface of said head portion so that said unintended relative movement between said anchor member and said receiver member is substantially limited.

8. An orthopedic implant apparatus comprising:
   a receiver member for receiving at least a part of a spinal rod, said receiver member having a lower opening and an internal chamber with a side wall, said receiver member further having at least one aperture in said side wall, and further including at least one friction member at least partially in at least one of said apertures, said friction member is comprised of a non-metallic elastomeric material; and
   an anchor member having a head portion and an anchor portion, said anchor member being movably connected to said receiver member, said head portion is comprised of a biocompatible material different from said elastomeric material and selected from the group consisting of a metallic material, a ceramic material and a hard plastic material, said biocompatible material of said head portion abutting said non-metallic elastomeric material of said friction member so that unintended relative movement of said anchor member and said receiver member is substantially limited; and wherein said receiver member has three said apertures, and wherein each said aperture has a respective friction member at least partially in a respective aperture, each of said friction members abutting said anchor member.

9. The apparatus of claim 8, wherein said apertures are substantially in the same plane.

10. The apparatus of claim 9, wherein said plane is substantially coplanar with a diameter of said head.

11. The apparatus of claim 8, wherein said apertures are substantially equiangularly spaced about said internal chamber.

12. An orthopedic implant apparatus comprising:
a receiver member for receiving at least a part of a spinal rod, said receiver member having a lower opening and an internal chamber with a side wall, said receiver member further having at least one aperture in said side wall, and further including at least one friction member at least partially in at least one of said apertures, wherein said friction member is substantially of a non-metallic biocompatible substance comprising a non-metallic elastomeric material; and
an anchor member having a head portion and an anchor portion, said anchor member being movably connected to said receiver member, said head portion including an external spherical-shaped surface, said non-metallic elastomeric material forming a distal end face of said friction member and abutting said external spherical-shaped surface of said head portion so that unintended relative movement of said anchor member and said receiver member is substantially limited.

13. An orthopedic implant apparatus comprising:
a receiver member for receiving at least a part of a spinal rod, said receiver member having a lower opening and an internal chamber with a side wall, said receiver member further having at least one aperture in said side wall, and further including at least one friction member at least partially in at least one of said apertures, wherein said friction member is substantially of a non-metallic biocompatible substance comprising a non-metallic elastomeric material; and
an anchor member having a head portion and an anchor portion, said anchor member being movably connected to said receiver member, said head portion including an external surface having a spherical-shaped portion abutting a distal end face of said friction member so that unintended relative movement of said anchor member and said receiver member is substantially limited; and
wherein said non-metallic elastomeric material is selected from the group consisting of a polymeric material, a rubber-based material, and a silicone-based material.

14. An orthopedic implant apparatus, comprising:
a first member having an internal chamber defining an internal surface, a friction member being fixedly placed on or in said internal surface, said friction member is comprised of a non-metallic elastomeric material; and
a second member including a portion defining an external surface positioned within said internal chamber and connected to and movable with respect to said first member with a portion of said external surface abutting said internal surface of said first member, said portion of said second member is comprised of a biocompatible material different from said elastomeric material and selected from the group consisting of a metallic material, a ceramic material and a hard plastic material, said non-metallic elastomeric material of said friction member abutting said external surface of said portion of said second member so that unintended relative movement of said second member and said first member is substantially limited.

15. The apparatus of claim 14, wherein said first member comprises a receiver member having a channel for receiving an orthopedic elongated member, and said second member comprises an anchor member with said portion comprising a head portion of said anchor member.

16. The apparatus of claim 15, wherein said anchor member is one of multi-axially movable, rotatable, and pivotable with respect to said receiver member.

17. The apparatus of claim 14, wherein said non-metallic elastomeric material is selected from the group consisting of a polymeric material, a rubber-based material, and a silicone-based material.

18. The apparatus of claim 14, wherein said biocompatible material comprises a metallic material.

19. The apparatus of claim 14, wherein said non-metallic elastomeric material forms a distal end face of said friction member and is positioned in abutment against said external surface of said portion of said second member so that said unintended relative movement between said second member and said first member is substantially limited.

20. The apparatus of claim 19, wherein said external surface of said portion of said second member includes a spherical-shaped surface with a portion of said spherical-shaped surface abutting said internal surface of said first member, said distal end face of said friction member positioned in abutment against said spherical-shaped surface of said second member so that said unintended relative movement between said second member and said first member is substantially limited.

21. The apparatus of claim 19, wherein said distal end face of said friction member comprises a part-spherical bead surface positioned in abutment against a spherical-shaped portion of said external surface of said second member so that said unintended relative movement between said second member and said first member is substantially limited.

22. An orthopedic implant apparatus, comprising:
a first member having an internal chamber defining an internal surface, a friction member being fixedly placed on or in said internal surface, said friction member is comprised of a non-metallic elastomeric material selected from the group consisting of a polymeric material, a rubber-based material, and a silicone-based material; and
a second member including a portion positioned within said internal chamber and connected to and movable with respect to said first member, said portion of said second member is comprised of a biocompatible material different from said elastomeric material and selected from the group consisting of a metallic material, a ceramic material and a hard plastic material, said biocompatible material of said portion of said second member abutting said non-metallic elastomeric material of said friction member so that unintended relative movement of said second member and said first member is substantially limited;
wherein said friction member is a substantially cylindrical member, and wherein said first member includes a substantially cylindrical aperture in which at least part of said friction member is fixed, and wherein an end portion of said friction member extends from said aperture with an end surface of said friction member abutting said portion of said second member to substantially limit said unintended relative movement.

23. The apparatus of claim 22, wherein said portion of said second member includes a spherical-shaped external surface with a portion of said spherical-shaped surface abutting said internal surface of said first member, said non-metallic elastomeric material forms said end surface of said friction member and is positioned in abutment against said spherical-shaped external surface of said second member to substantially limit said unintended relative movement.

24. An orthopedic implant apparatus comprising:
a receiver member for receiving at least a part of a spinal rod, said receiver member having a lower opening and an internal chamber with a side wall, said receiver member further having at least one aperture in said side wall, and further including at least one friction member at least partially in at least one of said apertures, said friction member is comprised of a non-metallic elastomeric material; and
an anchor member having a head portion and an anchor portion, said anchor member being movably connected to said receiver member, said head portion is comprised of a biocompatible material different from said elastomeric material and selected from the group consisting of a metallic material, a ceramic material and a hard plastic material, said biocompatible material of said head portion abutting said non-metallic elastomeric material of said friction member so that unintended relative movement of said anchor member and said receiver member is substantially limited; and
wherein said non-metallic elastomeric material is selected from the group consisting of a polymeric material, a rubber-based material, and a silicone-based material.

25. An orthopedic implant apparatus, comprising:
a first member having an internal chamber defining an internal surface, a friction member being fixedly placed on or in said internal surface, said friction member is comprised of a non-metallic elastomeric material; and
a second member including a portion positioned within said internal chamber and connected to and movable with respect to said first member, said portion of said second member is comprised of a biocompatible material different from said elastomeric material and selected from the group consisting of a metallic material, a ceramic material and a hard plastic material, said biocompatible material of said portion of said second member abutting said non-metallic elastomeric material of said friction member so that unintended relative movement of said second member and said first member is substantially limited; and
wherein said non-metallic elastomeric material is selected from the group consisting of a polymeric material, a rubber-based material, and a silicone-based material.

* * * * *